United States Patent
Hoffman et al.

(10) Patent No.: US 11,406,355 B2
(45) Date of Patent: Aug. 9, 2022

(54) HANDHELD MEDICAL INTERFACE FOR INTRALUMINAL DEVICE AND ASSOCIATED DEVICES SYSTEMS AND METHODS

(71) Applicant: KONINKLIJKE PHILIPS N.V., Eindhoven (NL)

(72) Inventors: Joseph James Hoffman, Sacramento, CA (US); Cesar Perez, Roseville, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 81 days.

(21) Appl. No.: 16/166,040

(22) Filed: Oct. 19, 2018

(65) Prior Publication Data

US 2019/0117191 A1 Apr. 25, 2019

Related U.S. Application Data

(60) Provisional application No. 62/574,610, filed on Oct. 19, 2017.

(51) Int. Cl.
*A61B 8/00* (2006.01)
*G16H 40/63* (2018.01)
(Continued)

(52) U.S. Cl.
CPC .......... *A61B 8/4416* (2013.01); *A61B 5/0084* (2013.01); *A61B 8/12* (2013.01);
(Continued)

(58) Field of Classification Search
USPC ....................................................... 600/301
See application file for complete search history.

(56) References Cited

U.S. PATENT DOCUMENTS

| 9,603,554 B2* | 3/2017 | Liang | A61B 8/0883 |
| 2003/0184462 A1* | 10/2003 | Parfitt | G05B 19/054 341/141 |

(Continued)

FOREIGN PATENT DOCUMENTS

| WO | 2017057009 A1 | 4/2017 |
| WO | 2019077141 A1 | 4/2018 |

(Continued)

OTHER PUBLICATIONS

International Search Report and Written Opinion, International Application No. PCT/EP2018/077607, dated Jan. 21, 2019.

*Primary Examiner* — Gary Jackson
*Assistant Examiner* — Anant A Gupta

(57) ABSTRACT

Intraluminal medical devices, systems and methods are provided. In one embodiment, an intraluminal medical system includes a handheld interface device in communication with an intraluminal device to be positioned within a body lumen of a patient. The intraluminal device includes a sensor configured to obtain physiology data associated with the body lumen. The handheld interface device includes a housing sized and shaped for handheld use, a controller core disposed within the housing and configured to control a plurality of sensor types respectively associated with a plurality of intraluminal devices, a computing core disposed within the housing, and a first display integrated in the housing. The controller core is operable to identify the sensor of the intraluminal device, and control the sensor to obtain the physiology data associated with the body lumen. The computing core is operable to process the physiology data using instructions associated with the identified sensor, wherein the computing core is further operable to process physiology data associated with the plurality of sensor types respectively using a plurality of modality specific instructions; and generate a graphical representation based on the (Continued)

physiology data. The first display is operable to display the graphical representation based on the physiology data.

17 Claims, 4 Drawing Sheets

(51) Int. Cl.
    *A61B 5/00*     (2006.01)
    *A61B 8/12*     (2006.01)
    *A61B 8/08*     (2006.01)
    *A61B 5/026*     (2006.01)

(52) U.S. Cl.
    CPC ............ *A61B 8/4488* (2013.01); *A61B 8/464* (2013.01); *A61B 8/5223* (2013.01); *A61B 8/5269* (2013.01); *A61B 8/54* (2013.01); *G16H 40/63* (2018.01); *A61B 5/0086* (2013.01); *A61B 5/026* (2013.01); *A61B 2562/0247* (2013.01); *A61B 2562/08* (2013.01)

(56) References Cited

U.S. PATENT DOCUMENTS

2004/0193068 A1* 9/2004 Burton ................ A61B 5/4812
    600/544
2005/0288799 A1* 12/2005 Brewer ................ H05K 7/1472
    700/1
2007/0016068 A1* 1/2007 Grunwald ............. A61B 5/742
    600/468
2009/0105795 A1* 4/2009 Minogue ........... A61N 1/36003
    607/148
2014/0275844 A1 9/2014 Hoseit et al.
2015/0120249 A1* 4/2015 Hernke ................ A61B 5/0205
    702/189
2015/0335257 A1* 11/2015 McNaughton ........... A61N 1/05
    607/116
2016/0157808 A1 6/2016 Merritt et al.
2017/0231709 A1* 8/2017 Gupta ................ A61B 17/1703
    600/424
2017/0281026 A1* 10/2017 Nick .................... A61B 5/7445
2017/0325748 A1* 11/2017 Natarajan ............ A61B 5/0024
2018/0095054 A1* 4/2018 Huo .................... G01N 27/4165

FOREIGN PATENT DOCUMENTS

WO     2019076731 A1     4/2019
WO     2019076986 A1     4/2019

* cited by examiner

HANDHELD MEDICAL INTERFACE FOR INTRALUMINAL DEVICE AND ASSOCIATED DEVICES SYSTEMS AND METHODS

TECHNICAL FIELD

The present disclosure relates generally to handheld medical system and, in particular, intraluminal medical device with a handheld interface device. For example, a handheld medical system can include a handheld interface device that can identify the type of the sensor of the intraluminal device, process the physiology data obtained by the sensor, and generate a graphical representation of the physiology data.

BACKGROUND

Catheters are widely used as diagnostic tools for assessing a diseased vessel, such as an artery, within the human body to determine the need for treatment, to guide the intervention, and/or to assess its effectiveness. A catheter including one or more sensors is passed into the vessel and guided to the area of interest. Conventionally, a user operates the catheter sensor at a large console, such as a desktop computer with a tower PC, monitor, keyboard, mouse, and/or other input device. In other instances, a heavy cart-based on system, with a tower PC, monitor, keyboard, mouse, and/or other input device is used. Respective electrical cables are used to connect the console and the intraluminal device to an interface component, which facilitates transmission of power and/or data signals between the catheter sensor and the console. The presence of numerous, lengthy cables, and large and heavy consoles can inhibit the flexibility that a user has during a medical procedure. This can reduce the efficiency of a medical workflow. Moreover, it typically takes several hours or days to appropriately install the conventional console-based system.

SUMMARY

Embodiments of the present disclosure provide a handheld medical system that includes an intraluminal device coupled to a handheld interface device. The intraluminal device is configured to be inserted into a body lumen of a patient and a sensor or sensors on the intraluminal device is operable to obtain physiology data from the body lumen. The handheld interface device includes a housing that houses a controller core, a computer core, an analog to digital converter, a signal conditioning circuit, and a display. The housing is shaped and sized for handheld use. The handheld interface device receives, conditions, and processes the physiology data from the intraluminal device, generates a graphical representation of the physiology data, and displays the graphical representation on the display.

In one embodiment, an intraluminal medical system includes a handheld interface device in communication with an intraluminal device configured to be positioned within a body lumen of a patient. The intraluminal device includes a sensor configured to obtain physiology data associated with the body lumen. The handheld interface device includes a housing sized and shaped for handheld use, a controller core disposed within the housing and configured to control a plurality of sensor types respectively associated with a plurality of intraluminal devices, a computing core disposed within the housing, and a first display integrated in the housing. The controller core is operable to identify the sensor of the intraluminal device, and control the sensor to obtain the physiology data associated with the body lumen. The computing core is operable to process the physiology data using instructions associated with the identified sensor, wherein the computing core is further operable to process physiology data associated with the plurality of sensor types respectively using a plurality of modality specific instructions; and generate a graphical representation based on the physiology data. The first display is operable to display the graphical representation based on the physiology data.

In some embodiment, the intraluminal medical system of the present disclosure further includes the intraluminal device. In some embodiments, the plurality of sensor types includes a plurality of intravascular ultrasound (IVUS) sensor types. In some implementations, the plurality of IVUS sensor types includes a plurality of transducer center frequencies. In some instances, the plurality of sensor types comprises an imaging sensor, an ultrasound transducer, an ultrasound transducer array, an optical sensor, a pressure sensor, and a flow sensor. In some embodiments, the intraluminal medical system of the present disclosure further includes a signal conditioning circuit disposed within the housing. The signal conditioning circuit can be coupled to the intraluminal device and operate to condition the physiology data from the intraluminal device.

In some embodiments, the intraluminal medical system of the present disclosure further includes an analog to digital converter (ADC) disposed within the housing. The ADC can be coupled to the signal conditioning circuit and operate to digitize the physiology data from the signal conditioning circuit. In some implementations, the controller core is further operable to configure the signal conditioning circuit based on a modality of the identified sensor. In some implementations, the controller core is further operable to configure the computing core based on the modality of the identified sensor. In some instances, the controller core is operable to identify the sensor of the intraluminal device by sending a sensing signal to the intraluminal device and measuring an impedance of the intraluminal device in response to the sensing signal. In some embodiments, the intraluminal medical system of the present disclosure further includes a communication module disposed within the housing. The communication module is operable to transmit the graphical representation of the physiology data to a second display apart from the medical system.

In another embodiment, a method of obtaining physiology data is provided. The method includes controlling, using a controller core disposed within a housing of a handheld interface device, a sensor of an intraluminal device positioned within a body lumen of a patient to obtain physiology data associated with the body lumen, wherein the controller core is configured to control a plurality of sensor types respectively associated with a plurality of intraluminal devices; identifying the sensor of the intraluminal device, using the controller core of the handheld interface device; processing, using a computing core disposed within the housing of the handheld interface device, the physiology data using instructions associated with the identified sensor, wherein the computing core is further operable to process physiology data associated with the plurality of sensor types respectively using a plurality of modality specific instructions; generating, using the computing core, a graphical representation based on the obtained physiology data; and displaying, using a first display integrated in the housing of the handheld interface device, the graphical representation of the physiology data.

In some embodiments, the method of the present disclosure further includes configuring, using the controller core, the computing core based on a modality of the identified sensor. In some embodiments, the method of the present disclosure further includes conditioning the physiology data, using a signal conditioning circuit disposed within the housing. In some implementations, the method of the present disclosure further includes configuring, using the controller core, the signal conditioning circuit based on a modality of the identified sensor. In some embodiments, the method of the present disclosure further includes digitizing the physiology data, using an analog to digital converter (ADC) disposed within the housing. In some embodiments, the method of the present disclosure further includes configuring, using the controller core, the ADC based on a modality of the identified sensor. In some implementations, the method of the present disclosure further includes transmitting, using a communication module disposed within the housing, the graphical representation of the physiology data to a second display apart from the handheld interface device. In some embodiments, the plurality of sensor types comprises a plurality of IVUS sensor types. In some instances, the plurality of IVUS sensor types comprises a plurality of transducer center frequencies.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
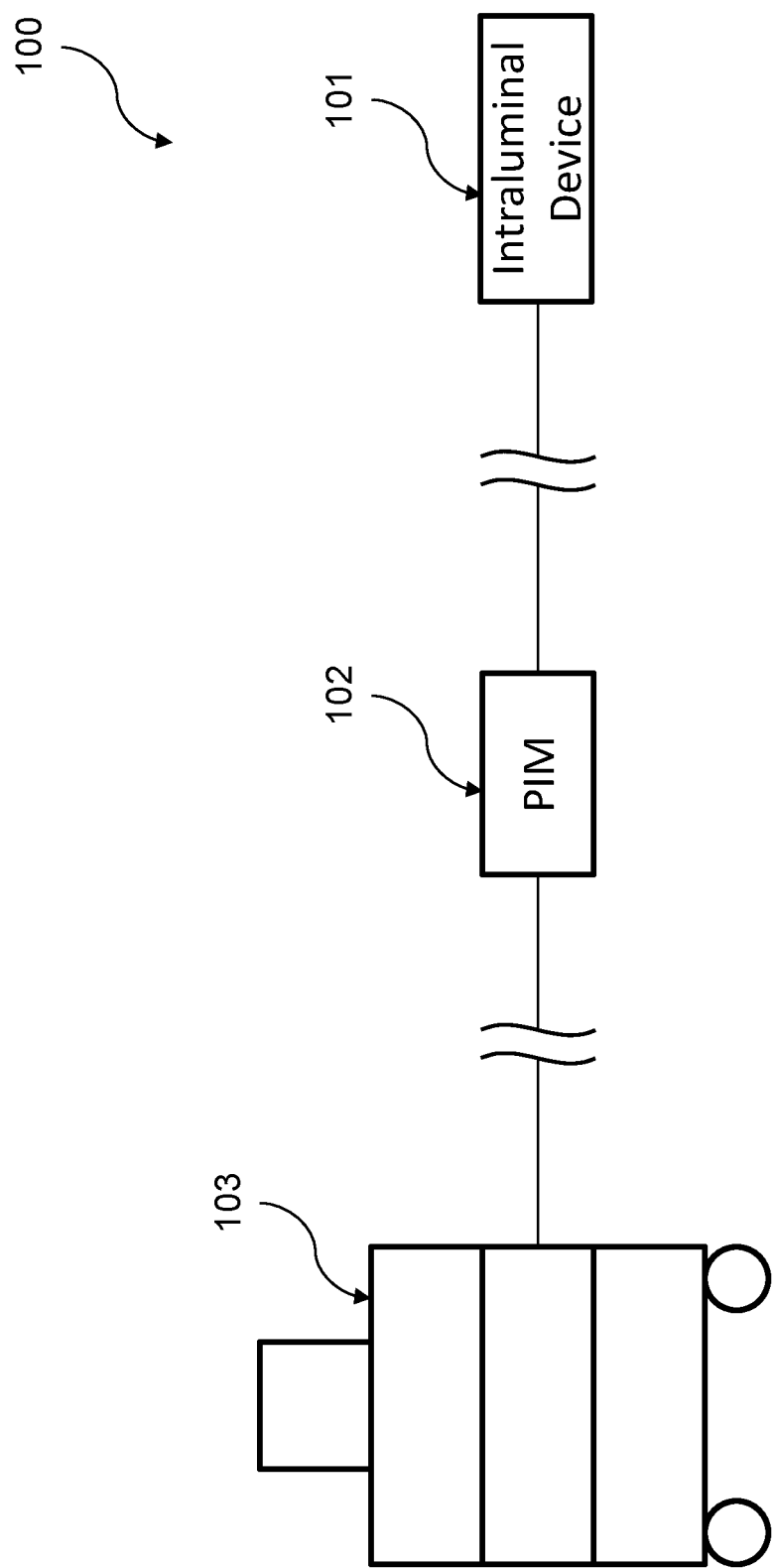
FIG. 1 is a diagrammatic schematic view of a prior-art intraluminal medical system.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of a prior-art intraluminal medical system 100. The prior-art intraluminal medical system 100 includes an intraluminal device 101, a patient interface module (PIM) 102 and a console 103. The intraluminal device 101 is connected to the PIM 102, which is connected to the console 103. The console 103 is usually bulky and may include wheels such that it can be wheeled around. For that reason, the prior-art intraluminal medical system 100 lacks mobility and takes up space in catheter labs.

Figure 2:
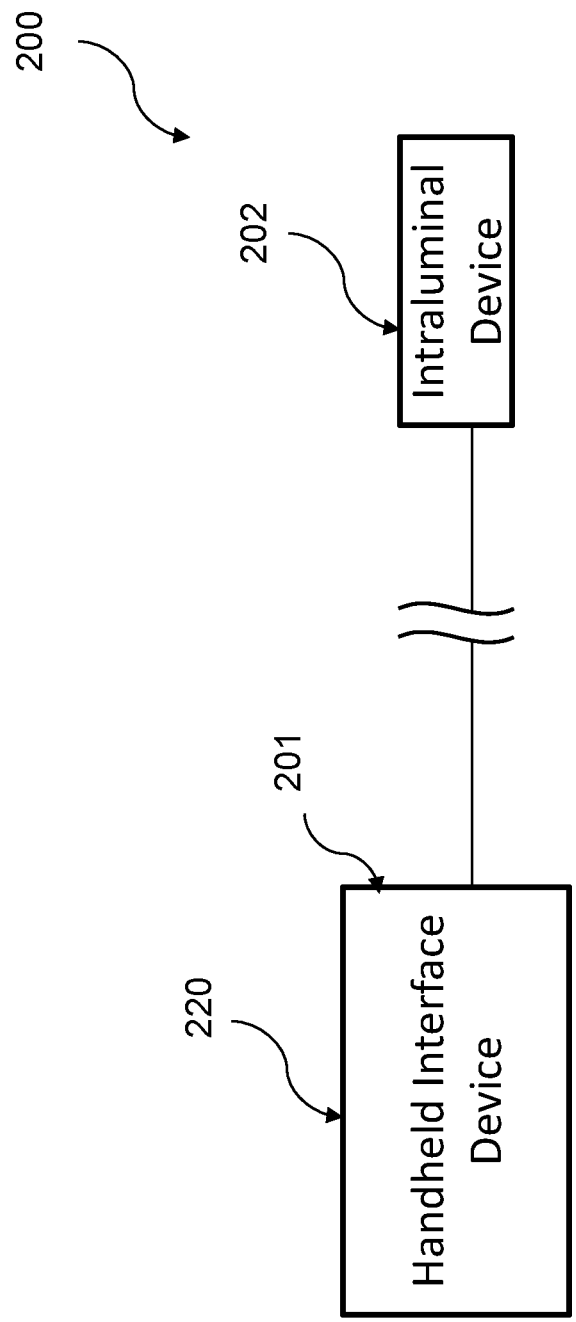
FIG. 2 is a functional block diagram of a medical system, according to aspects of the present disclosure.

Referring now to FIG. 2, shown therein is a functional block diagram of a medical system 200, according to aspects of the present disclosure. The medical system 200 includes an intraluminal device 202 and a handheld interface device 220. The handheld interface device 220 is approximately of the size of a tablet or a laptop and all of its physical components, such as circuitry, a display, and a user input device are disposed within or integrated with a housing 201. The physical components will be described in more detail in conjunction with FIG. 3 below. A user can hold the handheld interface device 220 with one hand. Alternative, in some embodiments, the handheld interface device 220 may include a stand that allows the handheld interface device 220 to be positioned on a horizontal surface or secured to a hospital bed rail. The intraluminal device 202 is configured to be inserted into a body lumen of a patient to obtain physiology data of the body lumen. In some embodiments, the physiology data obtained by the intraluminal device 202 include analog data and are too large to be transmitted via a digital cable. In those embodiments, the intraluminal device 202 is connected to the handheld interface device 220 via an analog cable or via a wireless connection. In the former case, the housing 201 includes at least a connection port for connecting the intraluminal device 202. In the latter case, both the handheld interface device 220 and the intraluminal device 202 have a wireless signal transceiver in compliance with the IEEE 802.11a, 802.11b/g/n and 802.11ac standards. In some embodiments, the wireless signal transceiver can utilize other wireless protocols, such Wireless Local Area Network (WLAN), Wireless Personal Area Network (WPAN), IrDA, Bluetooth, Zigbee, UWB, etc.

In some embodiments, the medical system 200 and/or the handheld interface device 220 can include features similar to those described in U.S. Patent Application No. 62/574,455, titled "DIGITAL ROTATIONAL PATIENT INTERFACE MODULE," filed Oct. 19, 2017, U.S. Patent Application No. 62/574,655, titled "WIRELESS DIGITAL PATIENT INTERFACE MODULE USING WIRELESS CHARGING," filed Oct. 19, 2017, U.S. Patent Application No. 62/574,687, titled "INTRALUMINAL DEVICE REUSE PREVENTION WITH PATIENT INTERFACE MODULE AND ASSOCIATED DEVICES, SYSTEMS, AND METHODS," filed Oct. 20, 2017 and U.S. Patent Application No. 62/574,835, titled "INTRALUMINAL MEDICAL SYSTEM WITH OVERLOADED CONNECTORS," filed Oct. 20, 2017, each of which is incorporated by reference in its entirety.

With the handheld interface device 220, the medical system 200 of the present disclosure is smaller, lightweight, portable, takes less space, and costs much less for installation. In addition, the medical system 200 includes fewer discrete components and is easy to install and set up. As a result, the medical system 200 of the present disclosure advantageously makes the catheter diagnosis tools more readily available to the clinician and more likely to be used in time-sensitive situations.

Figure 3:
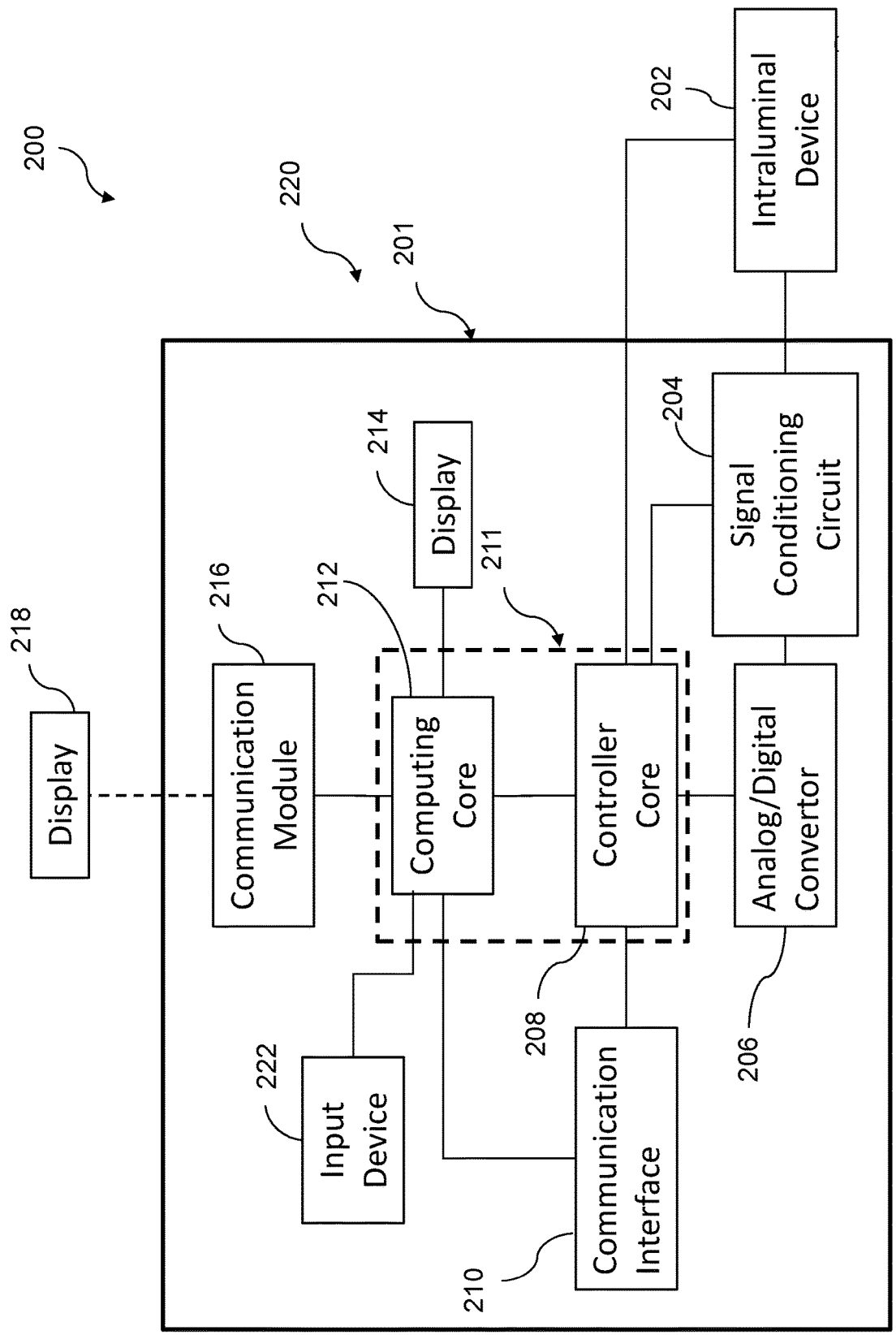
FIG. 3 is a diagrammatic schematic view of a medical system, according to aspects of the present disclosure.

Referring now to FIG. 3, shown there is a diagrammatic schematic view of the medical system 200. The handheld interface device 220 includes a housing 201. In some embodiments represented by FIG. 3, a signal conditioning circuit 204, an analog to digital converter (ADC) 206, a controller core 208, a computing core 212, an input device 222, and a display 214 are coupled to the housing 201. The housing can be any suitable shape including a volume (e.g., a height, a width, a depth, a radius, etc.) in which the signal conditioning circuit 204, the analog to digital converter (ADC) 206, the controller core 208, the computing core 212, the input device 222, and the display 214 are positioned, for example. In some embodiments, the display 214 can form a surface of the housing 201. The intraluminal device can include a flexible elongate member sized and shaped, structurally arranged, and/or otherwise configured to be positioned within a body lumen of a patient. For example, the intraluminal device can be an intravascular device configured to be positioned within a blood vessel of a patient, in some embodiments. The intraluminal device can include a flexible elongate member having a proximal portion and a distal portion. A sensor configured to obtain physiology data (e.g., imaging, pressure, flow, temperature, etc.) associated with the body lumen is disposed at the distal portion of the intraluminal device. In some embodiments, the intraluminal device 202 can be an intravascular ultrasound (IVUS) device, a near infrared (NIR) imaging device, an optical coherence tomography (OCT) device, an intravascular photoacoustic (IVPA) imaging device, a transesophageal echocardiography (TEE) device, an intracardiac echocardiography (ICE) device, or a flow rate catheter. For example, the intraluminal device 202 can be a phased array IVUS device, including an array of transducer circumferentially and/or annularly arranged around a longitudinal axis. In some embodiments, the intraluminal device 202 can be a rotational IVUS device, including a rotating drive cable that rotates an IVUS transducer. The intraluminal device 202 includes one or more sensors. For example, when the intraluminal device 202 is a NIR imaging device or an OCT device, the sensors of the intraluminal device 202 include imaging sensors, such as an optical sensor, or an infrared sensor. When the intraluminal device 202 is a flow rate catheter, the sensors are pressure sensors and flow rate sensors. In some embodiments, when the intraluminal device is an IVUS device, the sensors are ultrasound transducers, which can be a piezoelectric micromachined ultrasound transducer (PMUT), capacitive micromachined ultrasonic transducer (CMUT), single crystal, lead zirconate titanate (PZT), PZT composite, other suitable transducer type, combinations thereof, and/or arrays thereof. In some embodiments, when the intraluminal device 202 is an IVUS device, the intraluminal device 202 can include additional sensors, including a pressure sensor, a flow sensor, a temperature sensor, an optical fiber, a reflector, a mirror, a prism, and/or combinations thereof. In those embodiments, the additional sensors can be activated in the intraluminal device 202 in lieu of or in addition to the ultrasound transducers.

When in use, the intraluminal device 202 is connected to the handheld interface device 220. In some embodiments, the intraluminal device 202 is connected to the handheld interface device 220 via an analog signal cable. In some other embodiments, the intraluminal device 202 is connected to the handheld interface device 220 wirelessly. The controller core 208 can identify the modality or sensor type of the intraluminal device 202 and operating parameters of the intraluminal device, such as a center frequency of ultrasound transducers when the intraluminal device 202 is an IVUS device. Taking diagnostic IVUS imaging for example, the center frequency of the ultrasound transducer (s) can be between 2 MHz and 70 MHz, for example, including values such as 10 MHz, 20 MHz, 40 MHz, 45 MHz, 60 MHz, and/or other suitable values both larger and smaller. For example, lower frequencies (e.g., 10 MHz, 20 MHz) can advantageously penetrate further into the tissue around the body lumen. Higher frequencies (e.g., 45 MHz, 60 MHz) can be better suited to generate more detailed ultrasound images of the body lumen and/or fluids within the body lumen. In some embodiments, the frequency of the ultrasound transducer is tunable. For imaging, in some instances, the ultrasound transducer can be tuned to receive wavelengths associated with the center frequency and/or one or more harmonics of the center frequency. In some instances, the frequency of the emitted ultrasonic energy can be modified by the voltage of the applied electrical signal and/or the application of a biasing voltage to the ultrasound transducers. In some embodiments, the controller core 208 supplies the electrical signal and the biasing voltage to the ultrasound transducer. In some implementations, the handheld interface device 220 is configured to control a plurality of sensors associated with a plurality of intraluminal devices. The ability for the controller core 208 to identify the modality or sensor type of the intraluminal device 202 allows the medical system 200 to operate in different intraluminal modality. In some instances, ultrasound transducers with different center frequencies can be considered different sensor types. In some other instances, tunable ultrasound transducers can be considered a different type of sensors from fixed frequency ultrasound transducers.

In some embodiments, the handheld interface device 220 includes a "sleeping mode," in which the power consumption of the handheld interface device 220 is maintained at a low level and the controller core 208 does not transmit any control signals to the intraluminal device 202. In embodiments where the intraluminal device 202 is connected to the handheld interface device 220 by an analog signal cable, the controller core 208 can constantly or periodically output a sensing signal via the connection port. When the intraluminal device 202 is not connected to the handheld interface device, the sensing signal sees no impedance and the handheld interface device 220 stays in the "sleeping mode." However, when an intraluminal device 202 is connected to the handheld interface device 220, the sensing signal sees an impedance and the controller core 208 can detect the impedance and wake up from the "sleeping mode." In some embodiments, the controller core 208 can identify the modality/type and operating parameters of the intraluminal device 202 by comparing the impedance seen by the sensing signal to characteristic impedance values of a plurality of intraluminal devices 202 that are compatible with the handheld interface devices 220. The intraluminal device 202 can include a memory, such as an electrically erasable programmable read-only memory (EEPROM), in some embodiments. The EEPROM can store the modality/type and operating parameters of the intraluminal device 202 or encoded data representing the same. The controller core 208 can identify the modality/sensor type and operating parameters of the intraluminal device 202 by reading the EEPROM in such embodiments. Because the handheld interface device can identify the modality and sensor type of the intraluminal device 202, the handheld interface device 220 is configured to be operable with a plurality of intraluminal devices 220 (e.g., having different sensor types). In embodiments where the intraluminal device 202 is connected to the handheld interface device 220 wirelessly, the controller core 208 of the handheld interface device 220 can constantly or periodically broadcast a sensing signal or a beacon wirelessly. The intraluminal device 202 within a range of the sensing signal or beacon can respond the sensing signal or beacon by a linking signal. Once the handheld interface device 220 receives a linking signal, the controller core 208 can cause the computing core 212 to output a dialogue box to the display 214, asking a user for permission or confirmation to initiate connection with the intraluminal device 202. When the user permits or confirms connection with the intraluminal device 202, the handheld interface device 220 can wake up from the "sleeping mode" and connect to the intraluminal device 202.

After the controller core 208 identifies the modality/sensor type of the intraluminal device 202, the controller core 208 would configure the signal conditioning circuit 204, the ADC 206 and the computing core 212 based on the modality/sensor type and operating parameters of the intraluminal device 202. In some embodiments, the controller core 208 configures the signal conditioning circuit 204 by selecting a combination of amplifiers and band-pass filters suitable for the identified modality or sensor type of the intraluminal device 202. In some implementations, the controller core 208 configures the ADC 206 by changing parameters associated with the ADC 206. In some instances, the parameters may include a reference voltage fed to the ADC 206. In still some embodiments, the controller core 208 configures the computing core 212 by changing the set of instructions or algorithms to process the physiology data and to generate graphical representation of the physiology data. In some implementations, each modality or each sensor type of the intraluminal device 202 corresponds to a modality-specific or sensor-specific instructions or algorithms. The intraluminal device 202 is inserted into a body lumen of a patient. In response to control signal from the controller core 208, the sensors of the intraluminal device 202 obtain physiology data of the body lumen of the patient. The intraluminal device 202 then sends the obtained physiology data to the signal conditioning circuit 204. In some embodiments, the signal conditioning circuit 204 includes amplifiers, band-pass filters and other signal enhancing and/or noise reduction circuitry. In some instances, the medical system 200 can include structures disclosed in U.S. Patent Application No. 62/574,455, titled "DIGITAL ROTATIONAL PATIENT INTERFACE MODULE," filed Oct. 17, 2017, or U.S. Patent Application No. 62/574,655, titled "WIRELESS DIGITAL PATIENT INTERFACE MODULE USING WIRELESS CHARGING," filed Oct. 17, 2017, each of which is incorporated by reference in its entirety. The signal conditioning circuit 204 conditions the obtained physiology data and sends the conditioned physiology data to the ADC 206. The ADC 206 converts the conditioned physiology data from analog forms into digital forms. In some instances, the analog to digital conversion performed by the ADC 206 may be referred to herein as digitizing or digitization from time to time.

The digitized physiology data is then sent to the controller core 208. The controller core 208 can then encode the digitized physiology data for low-voltage different signaling (LVDS) transmission to the computing core 212. The LVDS transmission is not without its limit. In some instances, it can support physiology data transmission up to around 3 Gbit/s. In some embodiments illustrated in FIG. 3, the handheld interface device 220 further includes a communication interface 210. In some embodiments, the communication interface 210 is a physical layer device that can modulate digitized physiology data for transmission rate beyond 3 Gbit/s. In those embodiments, instead of sending the digitized physiology data to the computing core 212 directly via LVDS, the controller core 208 first sends the digitized physiology data to the communication interface 210. The communication interface 210 then modulates the digitized physiology data based on a communication protocol and transmits the modulated physiology data to the computing core 212. In some instances, the communication protocol includes the USB3.0 protocol and the 10 Gb Ethernet protocol. In implementations where the physiology data transmission rate is below 3 Gbit/s, the communication interface 210 is optional. However, in implementations where the physiology data transmission rate is beyond 3 Gbit/s, the communication interface 210 can improve the transmission rate and provides more satisfactory user experience.

In embodiments where the physiology data is modulated before transmission to the computing core 212, the computing core 212 demodulates the modulated physiology data before it processes the physiology data, generates a graphical representation of the physiology data, and outputs the graphical representation to the display 214 for display. In other embodiments where the digitized physiology data is transmitted to the computing core 212 by LVDS, the computing core 212 does not need to demodulate the received physiology data before processing the same. In some embodiments, the handheld interface device 220 may include an input device 222. In some instances, the input device 222 is a touch sensor integrated with the display 214. In some embodiments, the computing core 212 and the controller core 208 may be separate cores or separate groups of cores of one processor 211, such as a central processing unit (CPU). In some embodiments, the computing core 212 and/or the controller core 208 can be a field-programmable gate array (FPGA). In embodiments where the controller core 208 and the computing core 212 are parts of one processor, the handheld interface device 220 does not have the communication interface 210. In some embodiments, the handheld interface device 220 may further include a communication module 216, which can broadcast the physical representation of the physiology data to one or more remote display(s) 218. Different from display 214, which is integrated with the housing 201, the display 218 is apart from the handheld interface device 220. In some implementations, the display 218 is larger than display 214 and is configured to display the graphical representation in higher resolution or in more detail. In some embodiments, the handheld interface device 220 can communicate with a remote server or database by use of the communication module 216. For example, in response to a user input, the computing core 212 can cause the communication module 216 to initiate a connection with a remote server or a database so as to retrieve physiology data or imaging data of the patient.

The body lumen, as used herein, can be a vessel, such as a blood vessel. In various embodiments, the body lumen is an artery or a vein of a patient's vascular system, including cardiac vasculature, peripheral vasculature, neural vasculature, renal vasculature, and/or any other suitable anatomy/lumen inside the body. The body lumen can be tortuous in some instances. For example, the intraluminal device 202 may be used to examine any number of anatomical locations and tissue types, including without limitation, organs including the liver, heart, kidneys, gall bladder, pancreas, lungs, esophagus; ducts; intestines; nervous system structures including the brain, dural sac, spinal cord and peripheral nerves; the urinary tract; as well as valves within the blood, chambers or other parts of the heart, and/or other systems of the body. In addition to natural structures, the intraluminal device 202 may be used to examine man-made structures such as, but without limitation, heart valves, stents, shunts, filters and other devices.

Figure 4:
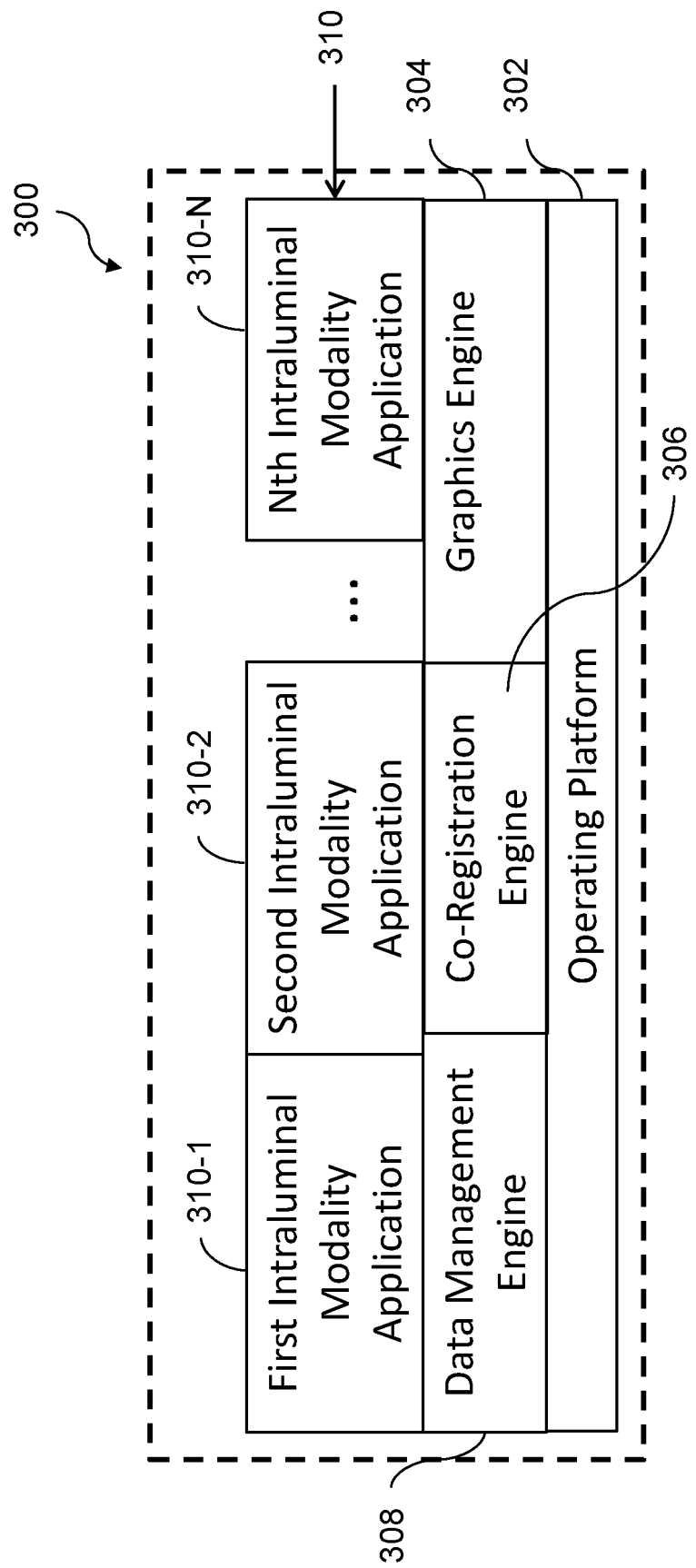
FIG. 4 is a functional block diagram of a software framework executing on the medical system, according to aspects of the present disclosure.

FIG. 4 is a functional block diagram of a software framework 300 executing on the medical system 200, according to aspects of the present disclosure. In some embodiments, the software framework 300 executes on the computing core 212. The software framework 300 includes a plurality of software layers that manage various aspects of the medical system 200 shown in FIGS. 2 and 3. For instance, an operating platform 302 undergirds the software framework 300 and provides the core functionality of the medical system 200. For instance, the operating platform 302 may manage power consumption and distribution of the medical system 200 and may also manage network connectivity, for example, connection via the communication module 216 to the display 218 or a remote server where the physiology data of patients are stored. Further, the software framework 300 may include a graphics engine 304 operable to process physiology data and generate graphic representation of the physiology data. Additionally, the software framework 300 includes a co-registration engine 306 operable to align, co-register or fuse physiology data obtained using different modality of intraluminal device 202. For example, flow rate or pressure data of a body lumen of a patient can be co-registered with IVUS imaging data obtained from the same body lumen of the patient. The software framework 300 also includes a data management engine 308 operable to download from a server and upload to a server physiology data and patient information of a patient. Further, the data management engine 308 is operable to assign a patient-specific identifier to the graphical representation of the physiology data of the patient such that the graphical representation of the patient's physiology data can be stored and filed according to the patient's identification. In some embodiments, the patient-specific identifier (also referred to as the patient identifier) can be a system-assigned patient number or a number shown on the patient's government-issued identification card.

The software framework 300 includes an application layer 310 in which applications associated with particular sensor types (e.g., different center frequencies from IVUS transducer and/or other intraluminal modalities, such as pressure, flow, OCT, etc.) may execute. The applications in the application layer 310 may be operable to generate graphical representations of the physiology data obtained from the body lumen of the patient. In embodiments shown in FIG. 4, the application layer 310 may include a first intraluminal modality application 310-1, a second intraluminal modality application 310-2, and the $n^{th}$ intraluminal modality application 310-N. Each of the applications is associated with a graphic user interface (GUI) geared towards displaying the graphical representation and relevant data. In some embodiments, at the GUI of each of the application, a user can check available physiology data for possible cross-modal co-registration. The different modalities of physiology data can be those obtained by a different intraluminal device or those stored in a remote server/database under the patient's identifier. For example, the first intraluminal modality application 310-1 can be specifically associated with an IVUS intraluminal device 202 with ultrasound transducers as its sensors, and the second intraluminal modality application 310-2 can be specifically associated with an OCT intraluminal device 202 with optical sensors. After the patient's body lumen is examined by use of the IVUS and OCT intraluminal devices, at either GUI of the first and second intraluminal modality applications, a user can select to fuse the graphical representations based on the IVUS and OCT physiology data. In some instances where the patient is subject to electrocardiogram (ECG) monitoring or three-dimensional (3D) angiography and the ECG and angiography data are stored in a server/database accessible by the co-registration engine 306, the application may present the user with options to co-register the IVUS or OCT data with the ECG or angiographic data.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal medical system, comprising:
a handheld interface device configured for communication with a plurality of different intraluminal devices configured to be positioned within a body lumen of a patient, wherein the plurality of different intraluminal devices respectively comprises a plurality of sensors corresponding to a plurality of sensor types and configured to obtain intraluminal data, the handheld interface device comprising:
a housing sized and shaped for handheld use;
an individual processor disposed within the housing, wherein the individual processor comprises a controller core and a computing core;
an analog to digital converter (ADC) disposed within the housing and configured to digitize the intraluminal data, wherein the ADC is in direct communication with the controller core; and
a first display integrated in the housing,
wherein the controller core is operable to:
identify a sensor of an intraluminal device in communication with the handheld interface device as one of the plurality of sensor types; and
configure the computing core and the ADC based on the identified sensor type; and
wherein the computing core is configured to execute a plurality of sensor-specific instructions associated with the plurality of sensor types,
wherein, to configure the computing core, the controller core is configured to change sensor-specific instructions executed by the computing core for each identified sensor type such that the computing core is operable to:
process the intraluminal data obtained by the sensor using the sensor-specific instructions for the identified sensor type; and
generate a graphical representation based on the intraluminal data using the sensor-specific instructions for the identified sensor type,
wherein, to configure the ADC, the controller core is configured to select, based on the identified sensor type, a sensor-specific reference voltage provided to the ADC to digitize the intraluminal data, and
wherein the first display is operable to display the graphical representation based on the intraluminal data.

2. The system of claim 1, wherein the plurality of sensor types comprises a plurality of IVUS sensor types.

3. The system of claim 2, wherein the plurality of IVUS sensor types comprises a plurality of transducer center frequencies.

4. The system of claim 1, wherein the plurality of sensor types is at least two of an imaging sensor, an ultrasound transducer, an ultrasound transducer array, an optical sensor, a pressure sensor, or a flow sensor.

5. The system of claim 1, furthering comprising:
a signal conditioning circuit disposed within the housing, the signal conditioning circuit coupled to the intraluminal device and operable to condition the obtained intraluminal data from the intraluminal device.

6. The system of claim 5, wherein the ADC is coupled to the signal conditioning circuit and operable to digitize the conditioned intraluminal data from the signal conditioning circuit.

7. The system of claim 5, wherein the controller core is operable to identify the sensor of the intraluminal device by sending a sensing signal to the intraluminal device and measuring an impedance of the intraluminal device in response to the sensing signal.

8. The system of claim 1, further comprising:
a communication module disposed within the housing, the communication module operable to transmit the graphical representation based on the obtained intraluminal data to a second display apart from the medical system.

9. The system of claim 1, wherein the computing core is further configured to:
co-register the intraluminal data obtained from at least two sensors of the plurality of sensors; and
generate a graphical representation based on the co-registered intraluminal data, and
wherein the first display is operable to display the graphical representation based on the co-registered intraluminal data.

10. The system of claim 1:
wherein the housing sized and shaped for handheld use is a single housing,
wherein the controller core and computing core are disposed within the single housing, and
wherein the first display is integrated in the single housing.

11. The system of claim 1, further comprising one or more of the plurality of different intraluminal devices.

12. The system of claim 1, wherein the plurality of sensor types comprise a plurality of intraluminal modalities, and wherein the plurality of sensor-specific instructions comprises a plurality of modality-specific instructions.

13. The system of claim 5, wherein the controller core is configured to select, based on the identified sensor type, a sensor-specific combination of amplifiers and band-pass filters.

14. The system of claim 1, wherein the controller core is configured to control the plurality of sensor types using a plurality of sensor-specific control signals such that the controller core controls the sensor of the intraluminal device to obtain the intraluminal data based on the identified sensor type.

15. The system of claim 1, wherein the individual processor comprises at least one of a central processing unit (CPU) or a field-programmable gate array (FPGA).

16. The system of claim 1, wherein the controller core configures the ADC by changing parameters associated with the ADC, wherein the parameters include the sensor-specific reference voltage provided to the ADC.

17. The system of claim 5, wherein controller core is operable to configure the signal conditioning circuit based on the identified sensor type, wherein the controller core configures the signal conditioning circuit by selecting a combination of amplifiers and band-pass filters suitable for the identified sensor type.

* * * * *